(12) United States Patent
Ding et al.

(10) Patent No.: US 11,931,010 B2
(45) Date of Patent: Mar. 19, 2024

(54) ENDOSCOPES AND METHODS OF TREATMENT

(71) Applicant: Covidien LP, Mansfield, MA (US)

(72) Inventors: Weijiang Ding, Shanghai (CN); Yuanxun Li, Shanghai (CN); Yancong Lu, Shanghai (CN)

(73) Assignee: Covidien LP, Mansfield, MA (US)

( * ) Notice: Subject to any disclaimer, the term of this patent is extended or adjusted under 35 U.S.C. 154(b) by 119 days.

(21) Appl. No.: 16/497,111

(22) PCT Filed: Mar. 24, 2017

(86) PCT No.: PCT/CN2017/078142
§ 371 (c)(1),
(2) Date: Sep. 24, 2019

(87) PCT Pub. No.: WO2018/170903
PCT Pub. Date: Sep. 27, 2018

(65) Prior Publication Data
US 2020/0016425 A1    Jan. 16, 2020

(51) Int. Cl.
*A61B 1/06*    (2006.01)
*A61B 1/00*    (2006.01)
(Continued)

(52) U.S. Cl.
CPC ........ *A61B 1/0676* (2013.01); *A61B 1/00006* (2013.01); *A61B 1/00066* (2013.01);
(Continued)

(58) Field of Classification Search
CPC ......... A61B 1/041; A61B 1/06; A61B 1/0605; A61B 1/0607; A61B 1/0615;
(Continued)

(56) References Cited

U.S. PATENT DOCUMENTS 4,584,988 A * 4/1986 Nishioka .................. A61B 1/07
600/177
5,377,669 A    1/1995 Schulz
(Continued)

FOREIGN PATENT DOCUMENTS

| CN | 1794944 A | 6/2006 |
| CN | 101874914 A | 11/2010 |

(Continued)

OTHER PUBLICATIONS

Machine English Translation of CN106178279A, Cong Wei; Liang Xudong; Liu Jinlin, Interposition-type ultraviolet light therapeutic instrument and control method thereof.*
(Continued)

*Primary Examiner* — Ryan N Henderson
(74) *Attorney, Agent, or Firm* — Carter, DeLuca & Farrell LLP

(57) ABSTRACT

An endoscope includes a handle, an elongated body extending distally from the handle and defining a longitudinal axis, a light source disposed within the distal portion of the elongated body and configured to illuminate tissue, and a therapeutic unit disposed within the distal portion of the elongated body and configured to treat tissue.

10 Claims, 7 Drawing Sheets

(51) Int. Cl.
*A61B 1/05* (2006.01)
*A61N 5/06* (2006.01)

(52) U.S. Cl.
CPC ............ *A61B 1/00087* (2013.01); *A61B 1/05* (2013.01); *A61B 1/0684* (2013.01); *A61N 5/0603* (2013.01); *A61N 2005/0652* (2013.01); *A61N 2005/0663* (2013.01)

(58) Field of Classification Search
CPC ... A61B 1/0623; A61B 1/0625; A61B 1/0627; A61B 1/063; A61B 1/0638; A61B 1/0646; A61B 1/0653; A61B 1/0655; A61B 1/0661; A61B 1/0669; A61B 1/0676; A61B 1/0684
See application file for complete search history.

(56) References Cited

U.S. PATENT DOCUMENTS

| | | | |
|---|---|---|---|
| 5,436,655 A * | 7/1995 | Hiyama | A61B 1/00194 348/45 |
| 5,718,663 A | 2/1998 | Wulfsberg | |
| 5,813,987 A * | 9/1998 | Modell | A61B 5/0062 600/476 |
| 6,204,523 B1 | 3/2001 | Carey et al. | |
| 6,260,994 B1 | 7/2001 | Matsumoto et al. | |
| 6,331,156 B1 | 12/2001 | Haefele et al. | |
| 6,449,006 B1 | 9/2002 | Shipp | |
| 6,488,619 B1 | 12/2002 | Miyanaga | |
| 6,503,196 B1 | 1/2003 | Kehr et al. | |
| 6,533,722 B2 * | 3/2003 | Nakashima | A61B 1/05 600/179 |
| 6,569,088 B2 * | 5/2003 | Koshikawa | A61B 1/00096 600/176 |
| 6,627,333 B2 | 9/2003 | Hatwar | |
| 6,656,112 B2 | 12/2003 | Miyanaga | |
| 6,696,703 B2 | 2/2004 | Mueller-Mach et al. | |
| 6,796,939 B1 | 9/2004 | Hirata et al. | |
| 6,821,246 B2 | 11/2004 | Kasel et al. | |
| 6,918,693 B2 | 7/2005 | Ota et al. | |
| 6,921,920 B2 | 7/2005 | Kazakevich | |
| 7,119,376 B1 | 10/2006 | Liu et al. | |
| 7,183,577 B2 | 2/2007 | Mueller-Mach et al. | |
| 7,275,931 B2 | 10/2007 | Katsuda et al. | |
| 7,413,543 B2 | 8/2008 | Banik et al. | |
| 7,442,167 B2 | 10/2008 | Dunki-Jacobs et al. | |
| 7,488,088 B2 | 2/2009 | Brukilacchio | |
| 7,585,273 B2 | 9/2009 | Adler et al. | |
| 7,635,330 B2 | 12/2009 | Kang et al. | |
| 7,668,450 B2 | 2/2010 | Todd et al. | |
| 7,691,056 B2 | 4/2010 | Hirata | |
| 7,738,940 B2 | 6/2010 | Shoji et al. | |
| 7,749,160 B2 | 7/2010 | Hirata | |
| 7,931,587 B2 | 4/2011 | Yoshino | |
| 7,968,901 B2 | 6/2011 | Yamashita et al. | |
| 7,976,459 B2 | 7/2011 | Laser | |
| 8,029,439 B2 | 10/2011 | Todd et al. | |
| 8,043,211 B2 | 10/2011 | Hirata | |
| 8,123,680 B2 | 2/2012 | Kato et al. | |
| 8,211,008 B2 | 7/2012 | Henzler | |
| 8,246,230 B2 | 8/2012 | Todd et al. | |
| 8,400,500 B2 | 3/2013 | Hirata | |
| 8,414,480 B2 | 4/2013 | Kendale et al. | |
| 8,449,457 B2 | 5/2013 | Aizenfeld et al. | |
| 8,480,566 B2 | 7/2013 | Farr | |
| 8,485,966 B2 * | 7/2013 | Robertson | A61B 1/00188 600/129 |
| 8,556,806 B2 | 10/2013 | Farr | |
| 8,591,408 B2 | 11/2013 | St. George et al. | |
| 8,622,896 B1 | 1/2014 | Termanini | |
| 8,670,028 B2 | 3/2014 | Takasaki | |
| 8,790,253 B2 | 7/2014 | Sunagawa et al. | |
| 8,801,255 B2 | 8/2014 | Kudo | |
| 8,878,920 B2 | 11/2014 | Ovod | |
| 9,259,140 B2 | 2/2016 | Hirosawa | |
| 9,270,919 B2 | 2/2016 | Amling et al. | |
| 9,271,630 B2 | 3/2016 | Amling et al. | |
| 9,271,637 B2 | 3/2016 | Farr | |
| 9,277,851 B2 | 3/2016 | Stuehle et al. | |
| 9,307,893 B2 | 4/2016 | Kennedy, II et al. | |
| 9,319,636 B2 | 4/2016 | King | |
| 9,357,902 B2 | 6/2016 | Amling et al. | |
| 9,398,839 B2 | 7/2016 | Rehe | |
| 9,408,525 B2 | 8/2016 | Dahmen | |
| 9,498,110 B2 | 11/2016 | Asatori | |
| 9,520,428 B2 | 12/2016 | Fujimori | |
| 9,525,852 B2 | 12/2016 | Wodnicki et al. | |
| 9,782,059 B2 | 10/2017 | Saito et al. | |
| 10,111,577 B2 | 10/2018 | Weber et al. | |
| 10,213,097 B2 | 2/2019 | Kohno et al. | |
| 10,275,905 B2 | 4/2019 | Yamaki | |
| 10,285,577 B2 | 5/2019 | Czupalla et al. | |
| 10,708,553 B2 * | 7/2020 | Sonoda | A61B 1/00006 |
| 10,952,600 B2 * | 3/2021 | Huang | A61B 1/128 |
| 2002/0184122 A1 | 12/2002 | Yamaguchi et al. | |
| 2005/0049462 A1 * | 3/2005 | Kanazawa | A61B 1/0605 600/176 |
| 2005/0075538 A1 | 4/2005 | Banik et al. | |
| 2005/0124858 A1 * | 6/2005 | Matsuzawa | A61B 1/041 600/176 |
| 2005/0203338 A1 * | 9/2005 | Couvillon, Jr. | A61B 1/00013 600/109 |
| 2006/0215406 A1 * | 9/2006 | Thrailkill | A61B 1/0638 362/249.06 |
| 2007/0173695 A1 | 7/2007 | Hirata | |
| 2007/0197873 A1 | 8/2007 | Birnkrant | |
| 2007/0225556 A1 | 9/2007 | Ortiz et al. | |
| 2007/0249904 A1 | 10/2007 | Amano et al. | |
| 2008/0045800 A2 * | 2/2008 | Farr | A61B 1/00179 600/179 |
| 2008/0064925 A1 * | 3/2008 | Gill | A61B 1/00142 600/109 |
| 2008/0077200 A1 * | 3/2008 | Bendett | A61N 5/0618 607/89 |
| 2008/0119740 A1 * | 5/2008 | Iddan | A61B 5/0084 356/300 |
| 2008/0158349 A1 * | 7/2008 | Miller | H04N 5/2256 348/82 |
| 2008/0200758 A1 | 8/2008 | Orbay et al. | |
| 2009/0058997 A1 | 3/2009 | Kato | |
| 2009/0154192 A1 | 6/2009 | Krattiger | |
| 2009/0247828 A1 | 10/2009 | Watanabe et al. | |
| 2010/0188493 A1 | 7/2010 | Kanzaki et al. | |
| 2010/0240953 A1 * | 9/2010 | Murakami | A61B 5/0084 600/109 |
| 2010/0286475 A1 * | 11/2010 | Robertson | A61B 1/00188 600/109 |
| 2010/0324632 A1 * | 12/2010 | Lim | A61N 5/0603 607/89 |
| 2011/0009694 A1 | 1/2011 | Schultz et al. | |
| 2011/0077465 A1 | 3/2011 | Mizuyoshi et al. | |
| 2011/0092772 A1 * | 4/2011 | Weber | A61B 1/128 600/178 |
| 2011/0118547 A1 * | 5/2011 | Erikawa | A61B 1/063 600/108 |
| 2011/0184244 A1 | 7/2011 | Kagaya et al. | |
| 2011/0263943 A1 * | 10/2011 | Yamaguchi | A61B 1/0638 600/178 |
| 2012/0041267 A1 * | 2/2012 | Benning | A61B 1/0655 600/180 |
| 2012/0071710 A1 * | 3/2012 | Gazdzinski | A61B 8/12 600/101 |
| 2012/0209072 A1 | 8/2012 | Oue et al. | |
| 2012/0320581 A1 | 12/2012 | Rogers et al. | |
| 2013/0131451 A1 | 5/2013 | Dillinger et al. | |
| 2013/0265798 A1 | 10/2013 | Kudo | |
| 2013/0285094 A1 | 10/2013 | Hsu et al. | |
| 2013/0300847 A1 | 11/2013 | Hashimoto | |
| 2013/0334577 A1 | 12/2013 | Ahn | |
| 2014/0121468 A1 * | 5/2014 | Eichenholz | A61B 1/0638 600/249 |

(56) References Cited

U.S. PATENT DOCUMENTS

| | | | |
|---|---|---|---|
| 2014/0128745 A1* | 5/2014 | Willis | A61B 5/4836 600/476 |
| 2014/0316198 A1 | 10/2014 | Krivopisk et al. | |
| 2014/0330081 A1 | 11/2014 | Imai | |
| 2015/0094530 A1* | 4/2015 | Moriya | F21V 5/04 600/103 |
| 2015/0202456 A1* | 7/2015 | Andersen | A61N 5/0601 604/20 |
| 2015/0222801 A1* | 8/2015 | Kresser | H04N 23/74 348/362 |
| 2015/0272422 A1* | 10/2015 | Aoyama | H04N 9/04559 348/68 |
| 2015/0272442 A1 | 10/2015 | Motafakker-Fard et al. | |
| 2015/0297069 A1 | 10/2015 | Coppersmith et al. | |
| 2015/0366443 A1* | 12/2015 | Liolios | A61B 1/0638 600/249 |
| 2016/0007833 A1* | 1/2016 | Huang | A61B 1/0676 600/109 |
| 2016/0029879 A1 | 2/2016 | Ishikawa | |
| 2016/0058277 A1 | 3/2016 | Selcho et al. | |
| 2016/0073861 A1 | 3/2016 | Kaneko | |
| 2016/0077008 A1* | 3/2016 | Takasu | G01J 3/0208 348/77 |
| 2016/0081533 A1 | 3/2016 | Couvillon, Jr. | |
| 2016/0105606 A1 | 4/2016 | Hikita et al. | |
| 2016/0106303 A1 | 4/2016 | Birnkrant et al. | |
| 2016/0106306 A1* | 4/2016 | Furuta | G02B 23/2461 600/176 |
| 2016/0124211 A1 | 5/2016 | Wieters et al. | |
| 2016/0166132 A1 | 6/2016 | Sasamoto et al. | |
| 2016/0174823 A1 | 6/2016 | Asatori et al. | |
| 2016/0210411 A1 | 7/2016 | Mentis | |
| 2016/0213230 A1 | 7/2016 | Adair et al. | |
| 2016/0217255 A1 | 7/2016 | Ukai et al. | |
| 2016/0345814 A1* | 12/2016 | Sidar | A61B 1/0684 |
| 2016/0353983 A1* | 12/2016 | Onoe | G02B 23/243 |
| 2017/0007095 A1 | 1/2017 | Kutsuma et al. | |
| 2017/0035511 A1 | 2/2017 | Itoh et al. | |
| 2017/0049312 A1* | 2/2017 | Seth | A61B 1/303 |
| 2017/0150873 A1* | 6/2017 | Tatebayashi | A61B 1/05 |
| 2017/0215714 A1* | 8/2017 | Shinji | H04N 23/56 |
| 2018/0098686 A1* | 4/2018 | Tamiya | A61B 1/0008 |
| 2019/0150725 A1* | 5/2019 | Ramanujam | A61B 1/0676 |
| 2019/0216325 A1* | 7/2019 | Ouyang | A61B 1/00096 |
| 2019/0306467 A1* | 10/2019 | Sonoda | G02B 23/24 |
| 2019/0388175 A1* | 12/2019 | Tatsuta | A61B 1/06 |
| 2021/0100438 A1* | 4/2021 | Ding | A61B 1/00096 |

FOREIGN PATENT DOCUMENTS

| | | |
|---|---|---|
| CN | 102697449 A | 10/2012 |
| CN | 105249919 A | 1/2016 |
| CN | 106178279 A | 12/2016 |
| CN | 106308727 A | 1/2017 |
| EP | 1911389 A1 | 4/2008 |
| EP | 2353493 A1 | 8/2011 |
| EP | 2407087 A2 | 1/2012 |
| JP | 2008117184 A | 5/2008 |
| WO | 2010123858 A2 | 10/2010 |
| WO | 2014004992 A1 | 1/2014 |
| WO | 2014195843 A2 | 12/2014 |
| WO | 2016017325 A1 | 2/2016 |
| WO | 2016088512 A1 | 6/2016 |
| WO | 2016117373 A1 | 7/2016 |
| WO | 2018170903 A1 | 9/2018 |
| WO | 2018170904 A1 | 9/2018 |
| WO | 2019157763 A1 | 8/2019 |

OTHER PUBLICATIONS

Extended European Search Report dated Dec. 7, 2020 corresponding to counterpart Patent Application EP 17901503.7.

International Search Report dated Dec. 27, 2017 and Written Opinion completed Dec. 21, 2017 corresponding to counterpart Int'l Patent Application PCT/CN2017/078142.

Partial European Search Report corresponding to EP 15 17 6036.0 dated Nov. 25, 2015.

Extended European Search Report corresponding to counterpart Int'l Appln. No. EP 15 17 6036.0, dated May 6, 2016.

European Office Action corresponding to counterpart Int'l Appln. No. EP 15 17 6036.0 dated Apr. 26, 2017.

Chinese First Office Action corresponding to counterpart Int'l Appln. No. CN 201510405306 dated Dec. 5, 2017.

Chinese Second Office Action corresponding to counterpart Patent Application CN 201510405306 dated Jul. 31, 2018.

Australian Examination Report No. 1 corresponding to counterpart Patent Application AU 2015203154 dated Mar. 13, 2019.

Written Opinion completed Oct. 24, 2018 corresponding to Int'l Patent Application PCT/CN2018/076912.

Chinese Office Action dated Dec. 2, 2020 corresponding to counterpart Patent Application CN 2020112702421630.

Chinese Second Office Action dated Aug. 18, 2021 corresponding to counterpart Patent Application CN 201780088884.2.

Chinese Third Office Action dated Feb. 18, 2022 corresponding to counterpart Patent Application CN 201780088884.2.

\* cited by examiner

ENDOSCOPES AND METHODS OF TREATMENT

CROSS-REFERENCE TO RELATED APPLICATIONS

This application is a U.S. National Stage Application filed under 35 U.S.C. § 371(a) which claims the benefit of and priority to International Patent Application Serial No. PCT/CN2017/078142, filed Mar. 24, 2017, the entire disclosure of which is incorporated by reference herein.

TECHNICAL FIELD

The present disclosure relates to endosurgical devices, systems and methods for observing internal features of a body during minimally invasive surgical procedures, and more particularly, to endoscopes including a therapeutic unit and methods of using endoscopes to treat tissue.

BACKGROUND

Endoscopes are introduced through an incision or a natural body orifice to observe internal features of a body. Conventional endoscopes are typically used for visualization during endoscopic or laparoscopic surgical procedures. During such surgical procedures, it is common for tissue to be bluntly or sharply dissected, ligated, and/or sealed. Infections or the like may occur after such surgical procedures due in part to the disruption of tissue.

To help minimize the effects of such infections or the like, postoperative procedures are typically performed. However, postoperative procedures use additional instruments, take additional time, and are thus costly. Accordingly, it may be beneficial to provide an endoscope that can both provide visualization of tissue and provide therapeutic functions to tissue.

SUMMARY

The present disclosure relates to an endoscope including a handle, an elongated body extending distally from the handle and defining a longitudinal axis, a light source disposed within the distal portion of the elongated body and configured to illuminate tissue, and a therapeutic unit disposed within the distal portion of the elongated body and configured to treat tissue.

In disclosed embodiments, the therapeutic unit includes a plurality of LED elements. It is further disclosed that the endoscope includes a controller disposed in electrical communication with the light source and with the therapeutic unit. It is also disclosed that the endoscope includes an image sensor disposed within the distal portion of the elongated body and configured to capture a plurality of images.

According to aspects of the present disclosure, the therapeutic unit produces light energy. It is disclosed that the therapeutic unit is configured to focus the light energy on an area of tissue that is smaller than an area of tissue illuminated by the light source. It is further disclosed that the therapeutic unit includes a light emitting element and a lens. In embodiments, the lens includes a proximal surface and a distal surface. The proximal surface is disposed at first angle with respect to a first axis, and the distal surface disposed at a second angle with respect to the second axis. The first angle is between about 5° and about 15°, the second angle is between about 5° and about 15°, and the first axis is perpendicular to the longitudinal axis.

In disclosed embodiments, the therapeutic unit is configured to emit light having a wavelength raging from about 500 nm to about 650 nm. In embodiments, the therapeutic unit includes one red light, one blue light and one green light.

The present disclosure also relates to a method of treating tissue including positioning an endoscope adjacent tissue, illuminating the tissue using a light source of the endoscope, and treating the tissue using a therapeutic unit of the endoscope.

In disclosed embodiments of the method, illuminating the tissue using the light source includes illuminating a first area of tissue. Additionally, treating the tissue using the therapeutic unit includes focusing light energy on a second area of tissue. The second area of tissue is smaller than the first area of tissue.

In further disclosed embodiments of the method, treating the tissue using the therapeutic unit includes emitting light having a wavelength raging from about 500 nm to about 600 nm from the therapeutic unit to, for example, coagulate blood within the tissue, emitting light having a wavelength of about 570 nm from the therapeutic unit to induce fresh blood cells in the tissue to, for example, produce fluorescence, or emitting light having a wavelength of about 650 nm from the therapeutic unit to, for example, kill gangrene cells within the tissue.

Further details and aspects of various embodiments of the present disclosure are described in more detail below with reference to the appended figures.

BRIEF DESCRIPTION OF THE DRAWINGS

Embodiments of the present disclosure are described herein with reference to the accompanying drawings, wherein.

DETAILED DESCRIPTION OF EMBODIMENTS

Figure 1:
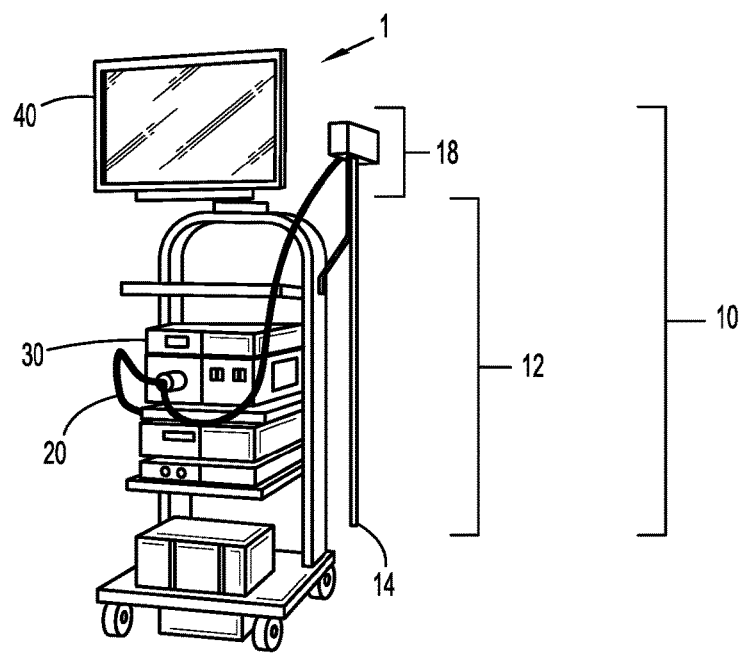
FIG. 1 is a front, perspective view of an endoscope system of the prior art.

Embodiments of the presently disclosed endoscopes and methods of treatment are described in detail with reference to the drawings, in which like reference numerals designate identical or corresponding elements in each of the several views. As used herein, the term "distal" refers to that portion of a structure that is farther from a user, while the term "proximal" refers to that portion of a structure that is closer to the user. The term "clinician" refers to a doctor, nurse, or other care provider and may include support personnel. The term "about" shall be understood as a word of approximation that takes into account relatively little to no variation in a modified term (e.g., differing by less than 2%).

Figure 2:
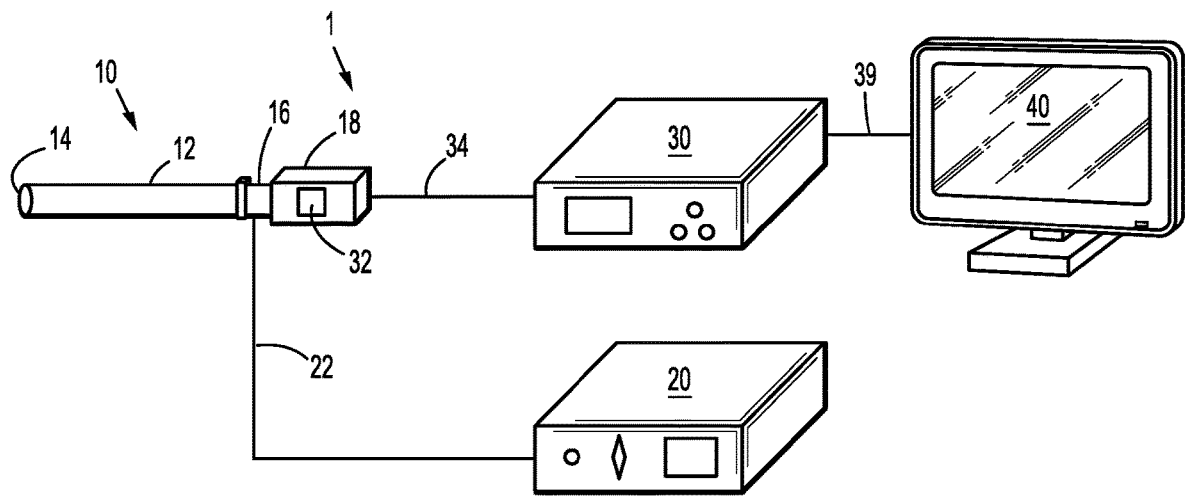
FIG. 2 is front, perspective view illustrating a schematic configuration of the endoscope system of FIG. 1.
Figure 3:
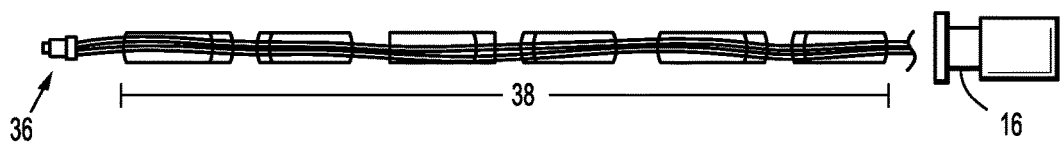
FIG. 3 is a side view illustrating a schematic configuration of an optical system of the endoscope system of FIG. 1.

Referring initially to FIGS. 1-3, a prior art endoscope system 1 includes an endoscope 10, a light source 20, a video system 30, and a display device 40. The light source 20, such as an LED/Xenon light source, is connected to the endoscope 10 via a fiber guide 22 that is operatively coupled to the light source 20 and to an endocoupler 16 disposed on, or adjacent to, a handle 18 of the endoscope 10. The fiber guide 22 includes, for example, fiber optic cable which extends through the elongated body 12 of the endoscope 10 and terminates at a distal end 14 of the endoscope 10. Accordingly, light is transmitted from the light source 20, through the fiber guide 22, and emitted out the distal end 14 of the endoscope 10 toward a targeted internal feature, such as tissue or an organ, of a body of a patient. As the light transmission pathway in such a configuration is relatively long, for example, the fiber guide 22 may be about 1.0 m to about 1.5 m in length, only about 15% (or less) of the light flux emitted from the light source 20 is outputted from the distal end 14 of the endoscope 10.

The video system 30 is operatively connected to an image sensor 32 mounted to, or disposed within, the handle 18 of the endoscope 10 via a data cable 34. An objective lens 36 is disposed at the distal end 14 of the elongated body 12 of the endoscope 10 and a series of spaced-apart, relay lenses 38, such as rod lenses, are positioned along the length of the elongated body 12 between the objective lens 36 and the image sensor 32. Images captured by the objective lens 36 are forwarded through the elongated body 12 of the endoscope 10 via the relay lenses 38 to the image sensor 32, which are then communicated to the video system 30 for processing and output to the display device 40 via cable 39.

The image sensor 32 is located within, or mounted to, the handle 18 of the endoscope 10, which can be up to about 30 cm away from the distal end 14 of the endoscope 10. Due to this relatively long distance, there is loss of image information in the image retrieval pathway as it is difficult to get a high quality image at every point along the whole working distance of the relay lenses 38. Moreover, due to light loss on the relay lenses 38, the objective lens 36 cannot include a small aperture. Therefore, the depth of field is limited and a focusing module (not shown) is typically utilized in the endocoupler 16 to set the objective lens 36 to a desired focal point, which a clinician adjusts when moving the endoscope 10 during a surgical procedure. Also, rotation of the fiber guide 22 will also rotate the relay lenses 38, which changes the viewing angle during use, and the fiber guide 22 also tends to fall due to the force of gravity. Accordingly, a clinician needs to adjust and/or hold the fiber guide 22 during use to keep the view stable, which is inconvenient during operation.

Figure 4:
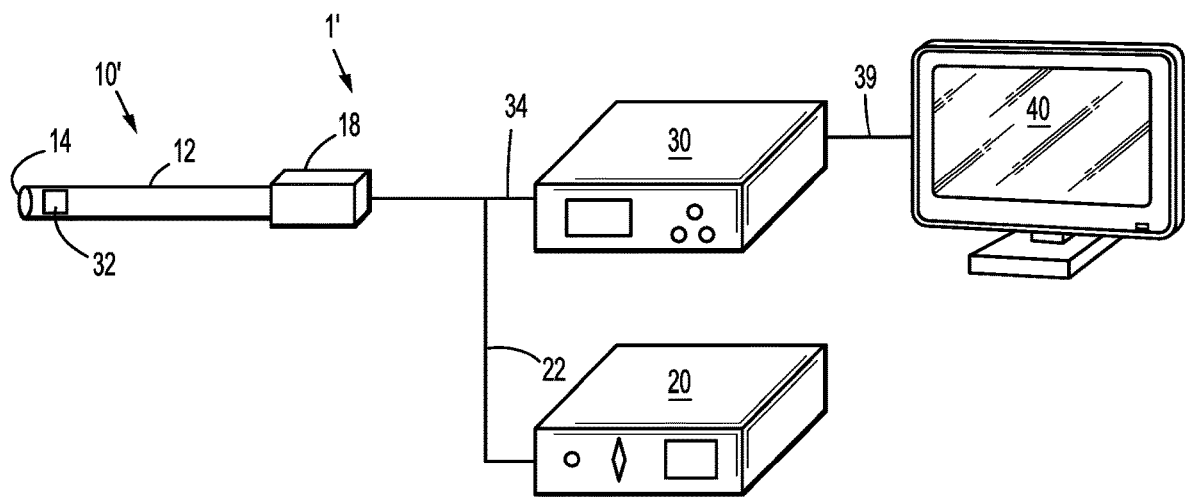
FIG. 4 is a front, perspective view illustrating a schematic configuration of another endoscope system of the prior art.
Figure 5:
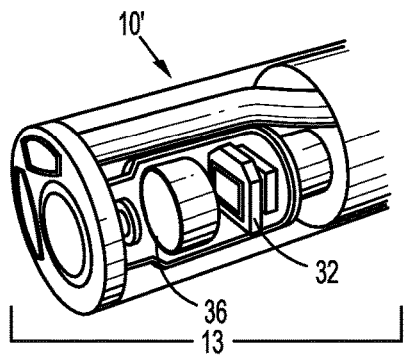
FIG. 5 is a perspective, partial cutaway view illustrating a schematic configuration of a distal end of an endoscope of the endoscope system of FIG. 4.

As shown in FIGS. 4 and 5, another prior art endoscope system 1', which is substantially similar to endoscope system 1 and therefore will only be described with respect to the differences therebetween, includes the image sensor 32 in a distal portion 13 of the elongated body 12 of the endoscope 10' such that the image retrieval pathway between the objective lens 36 and the image sensor 32 is shorter than that of the endoscope system 1. The endoscope system 1' adopts the same light transmission pathway as that of the endoscope system 1 (e.g., from the light source 20 and through the fiber guide 22), and thus light consumption on transmission is still large. However, the fiber guide 22 may be integrated with the data cable 34, thereby making the endoscope 10' easier to operate as a clinician does not need to adjust the fiber guide 22 during use.

Figure 6:
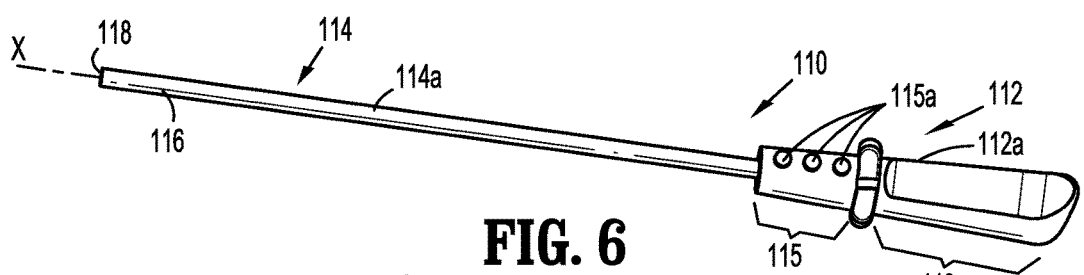
FIG. 6 is a perspective view of an endoscope in accordance with embodiments of the present disclosure.
Figure 7:
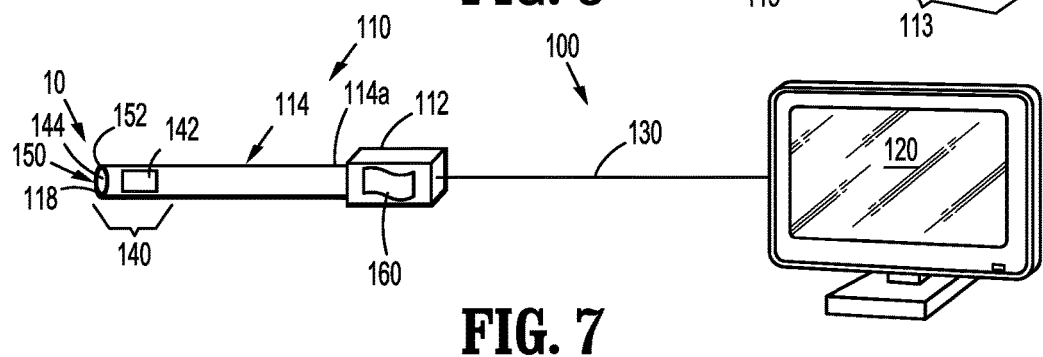
FIG. 7 is a schematic configuration of an endoscope system in accordance with an embodiment of the present disclosure.
Figure 8:
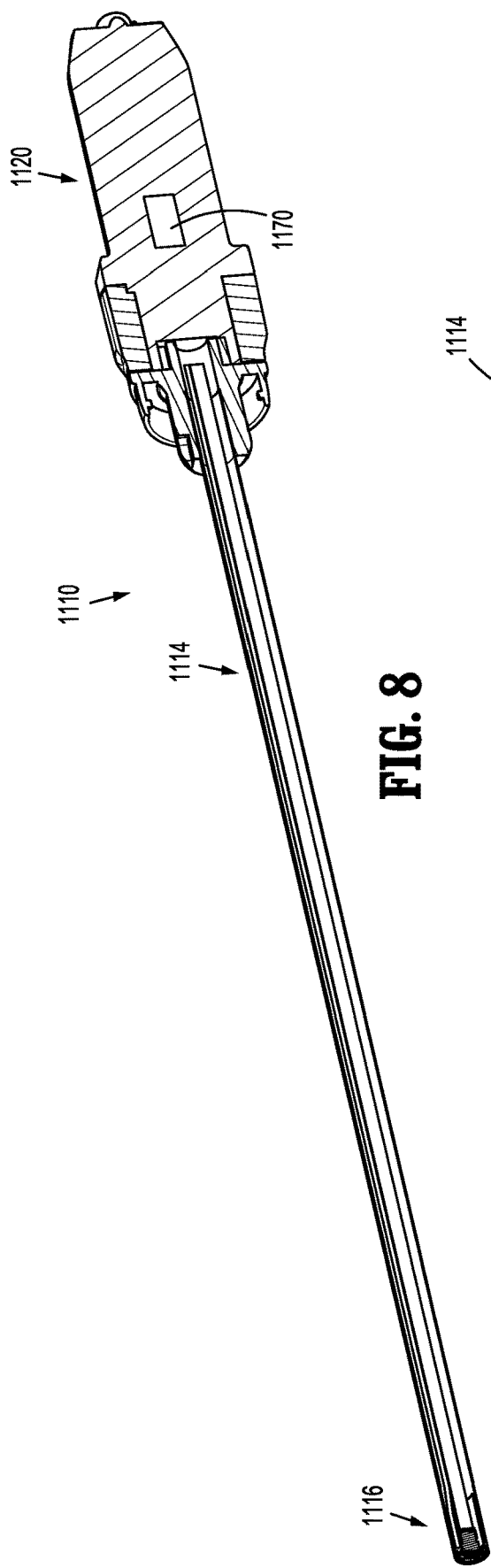
FIG. 8 is a longitudinal cross-sectional view of an endoscope in accordance with an embodiment of the present disclosure.
Figure 9:
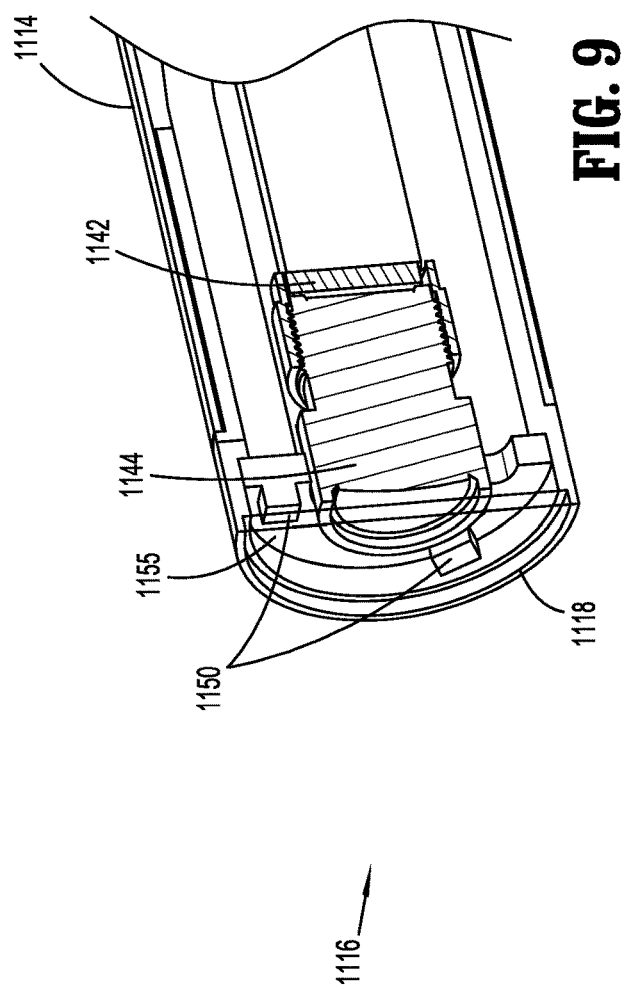
FIG. 9 is an enlarged view of a distal portion of the endoscope of FIG. 8.

Referring now to FIGS. 6 and 7, an endoscope system 100 of the present disclosure includes an endoscope 110, a display 120, and a cable 130 connecting the endoscope 110 and the display 120. A camera 140, a light source 150, and an integrated processor 160 are contained within the endoscope 110.

The endoscope 110 includes a handle 112 and an elongated body 114 having a cylindrical wall 114a extending distally from the handle 112 and defines a longitudinal axis "x." The elongated body 114 includes a distal portion 116 terminating at a distal end or tip 118. The handle 112 includes a handle housing 112a including a grip portion 113 for handling by a clinician and a control portion 115 including actuating elements 115a (e.g., buttons, switches etc.) for functional control of the endoscope 110.

With reference to FIGS. 6 and 7, the camera 140 is disposed within the elongated body 114 of the endoscope 110. The camera 140 includes an image sensor 142 disposed within the distal portion 116 of the elongated body 114 at a location proximal of a lens 144 that is positioned at the distal end 118 of elongated body 114. The image sensor 142 may be a charge-coupled device (CCD), a complementary metal-oxide-semiconductor (CMOS), or a hybrid thereof. In embodiments, the image sensor 142 is a highly sensitive, backside illuminated sensor (BSI). In embodiments, the lighting flux required by the image sensor 142 may be up to about 20 lm.

As the image retrieval pathway is shortened over that of traditional endoscope systems (e.g., FIG. 1) and the need for relay lenses is eliminated, the depth of field can be expanded and optimized. Accordingly, the lens 144 may include a depth of field from about 20 mm to about 110 mm with optimized image quality and a field-of-view of about 100 degrees. In embodiments, the lens 144 is a focus free lens. As compared to traditional endoscopes, a focus free lens relies on depth of field to produce sharp images and thus, eliminates the need to determine the correct focusing distance and setting the lens to that focal point. Accordingly, the aperture of the lens 144 can be relatively small, taking up less space at the distal end 118 of the elongated body 114. In embodiments, the outer diameter of the lens 144 is up to about 6 mm.

The light source 150 is disposed at the distal end 118 of the endoscope 110. Light source 150 includes one or more high efficiency light emitting elements 152, such as light-emitting diodes (LED) arranged in an annular ring around the lens 144 to ensure adequate and even light distribution. In embodiments, the light emitting elements 152 have a luminous efficacy of up to about 80 lm/W (lumen/watt). As compared to traditional endoscopes, the light source of the present disclosure reduces or eliminates the need for the use of an external light source and fiber guide, which can lower the cost of the endoscope system, simplify the endoscope system structure, and reduce light consumption and/or light distortion during light transmission. Although light emitting elements 152 may be efficient and produce less heat than other types of lighting, light emitting elements 152 still produce some heat, which can degrade the quality of the image, for instance.

Various endoscopes and methods to manage, reduce and/or dissipate the heat output from the light source are disclosed in corresponding International Patent Application Serial No. PCT/CN2017/078143, filed on Mar. 24, 2017, the entire contents of which are incorporated by reference herein. Other endoscopes that include a passive thermal control system are disclosed in U.S. Patent Application Publication No. 2016/0007833, filed on Jun. 3, 2015, the entire contents of which being incorporated by reference herein.

With particular reference to FIGS. 8-15, an embodiment of an endoscope is shown and is generally referenced by character 1110. Endoscope 1110 is a laparoscope visualization system that includes a therapeutic unit for treating tissue.

Endoscope 1110 is shown in FIGS. 8-13 and includes a handle 1120 and an elongated portion 1114 extending distally from the handle 1120. A distal portion 1116 of the elongated portion 1114 includes an image sensor 1142, a lens 1144, a lens barrel 1146, a protective window 1147, a light source (e.g., LED light emitting elements) 1150, a therapeutic unit 1160 (e.g., LED light emitting elements or other sources of light), a sensor substrate 1180, and a light source substrate 1190. Distal portion 1116 of elongated portion 1114 terminates in a distal end 1118.

Figure 10:
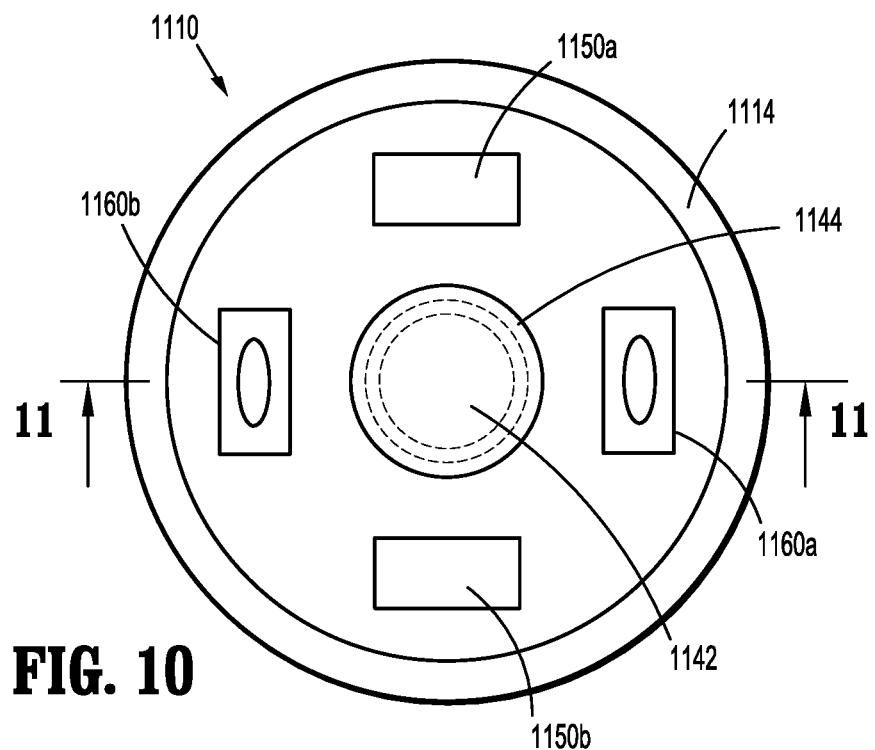
FIG. 10 is a schematic transverse, cross-sectional view of the distal portion of the endoscope of FIGS. 8 and 9.

In the embodiment illustrated in FIG. 10, light source 1150 includes two LED light emitting elements 1150a and 1150b, and therapeutic unit 1160 includes two LED light emitting elements 1160a and 1160b. In the embodiment illustrated in FIG. 13, light source 1150 includes three LED light emitting elements 1150a, 1150b and 1150c, and therapeutic unit 1160 includes three LED light emitting elements 1160a, 1160b and 1160c. It is also contemplated and within the scope of the present disclosure for more or fewer LED light emitting elements of light source 1150 and therapeutic unit 1160 to be used in connection with endoscope 1110. Additionally, LED light emitting elements of light source 1150 and therapeutic unit 1160 may be any combination of white, red, green and blue light emitting elements, for example. For instance, it is envisioned that one LED light emitting element 1160a is red, one LED light emitting element 1160b is green, and the other LED light emitting element 1160c is blue for providing various types of therapy. Further details of LED light emitting elements of therapeutic unit 1160 are discussed below.

Figure 11:
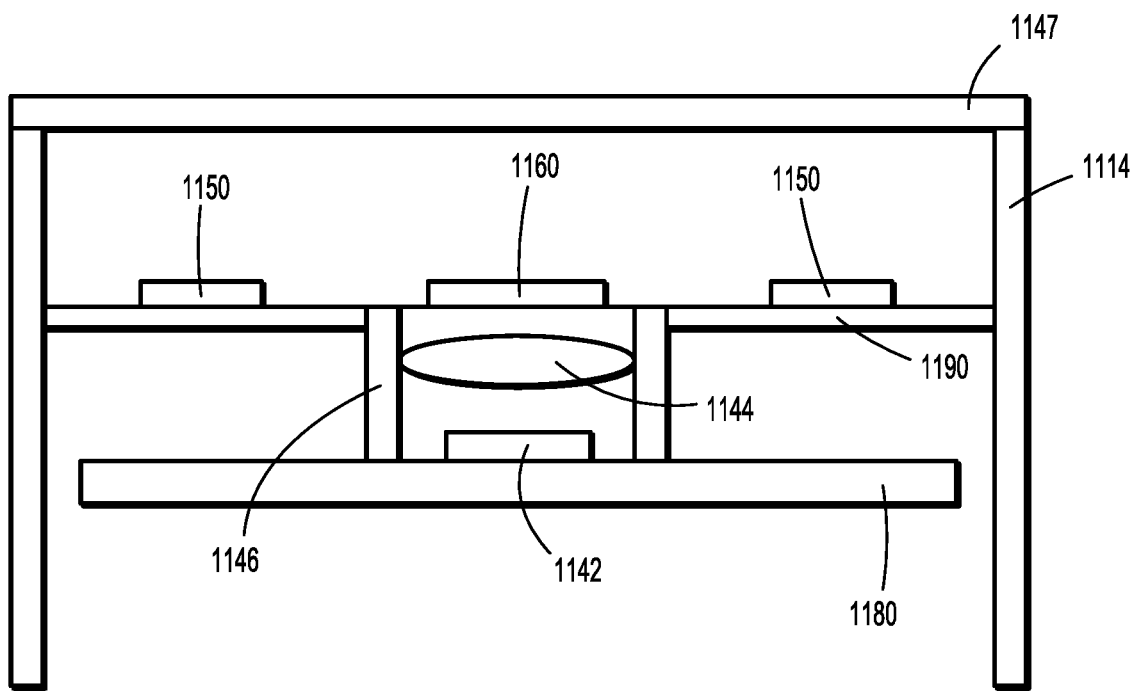
FIG. 11 is a schematic cross-sectional view of the distal portion of the endoscope of FIGS. 8-10 taken along line 11-11 of FIG. 10.
Figure 13:
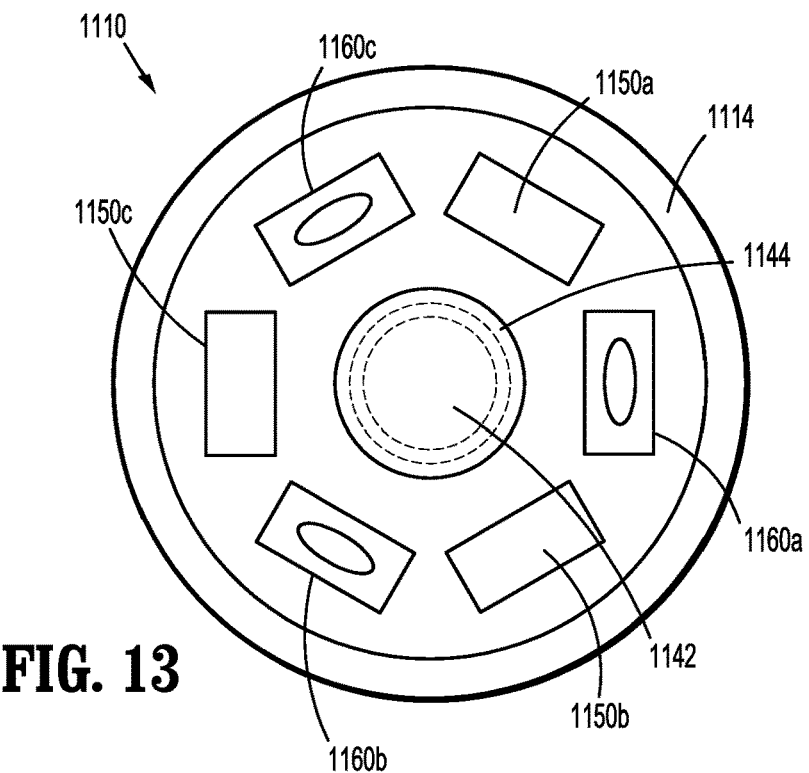
FIG. 13 is a schematic transverse, cross-sectional view of the distal portion of an endoscope in accordance with an embodiment of the present disclosure.
Figure 14:
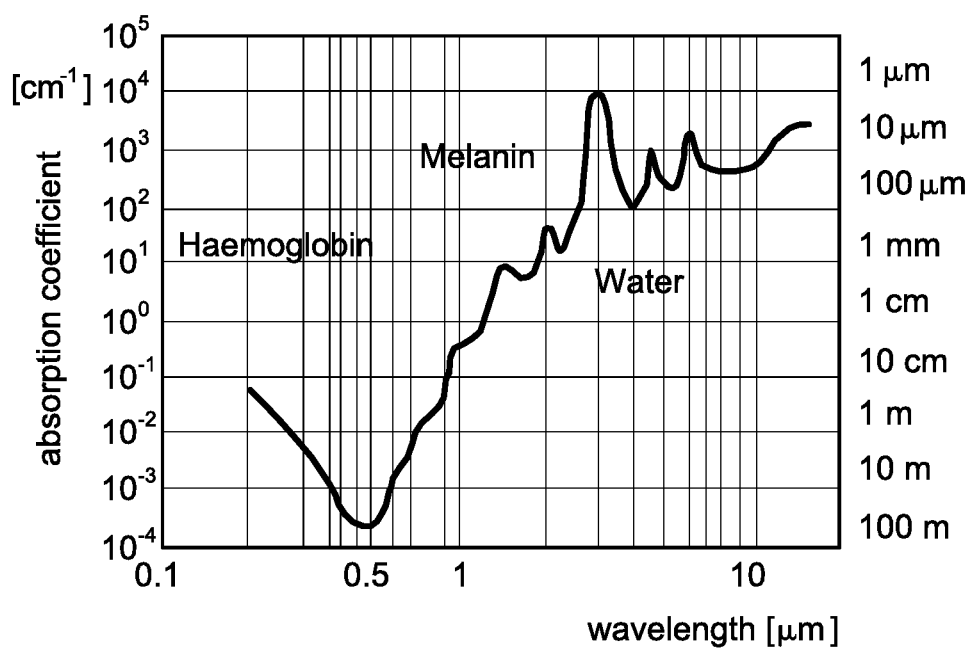
FIGS. 14 and 15 are graphs illustrating the relationship between absorption and wavelength of light.
Figure 15:
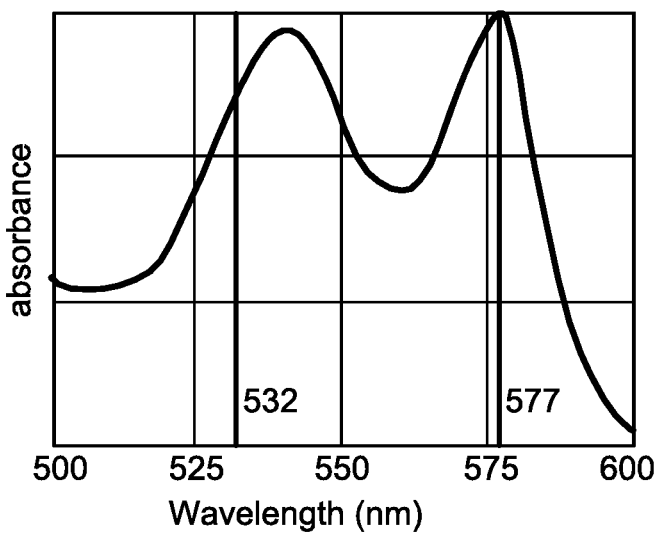

With particular reference to FIGS. 10, 11 and 13, LED light emitting elements 1150a-1150c of light source 1150 and LED light emitting elements 1160a-1160c of therapeutic unit 1160 are positioned radially outwardly of lens 1144 in an alternating pattern, and are engaged with (e.g., affixed to) light source substrate 1190, which is disposed distally of lens 1144. Sensor substrate 1180 is positioned proximally of lens 1144, and lens barrel 1146 extends distally from image sensor 1142 and from sensor substrate 1180. Lens 1144 is disposed within lens barrel 1146. Image sensor 1142 is engaged with or connected to (e.g., affixed to) sensor substrate 1180.

In embodiments, a processor 1155 is engaged with or connected to light source 1150 and therapeutic unit 1160, and is in electrical communication with a controller 1170 disposed within handle 1120.

In embodiments where endoscope 1110 includes controller 1170, controller 1170 is electrically connected to sensor substrate 1180 and light source substrate 1190 via cables, for example. The engagement between sensor substrate 1180 and image sensor 1142 results in an electrical connection between controller 1170 and image sensor 1142, and the engagement between light source substrate 1190 and light source 1150 and therapeutic unit 1160 results in an electrical connection between controller 1170, light source 1150 and therapeutic unit 1160.

Figure 12:
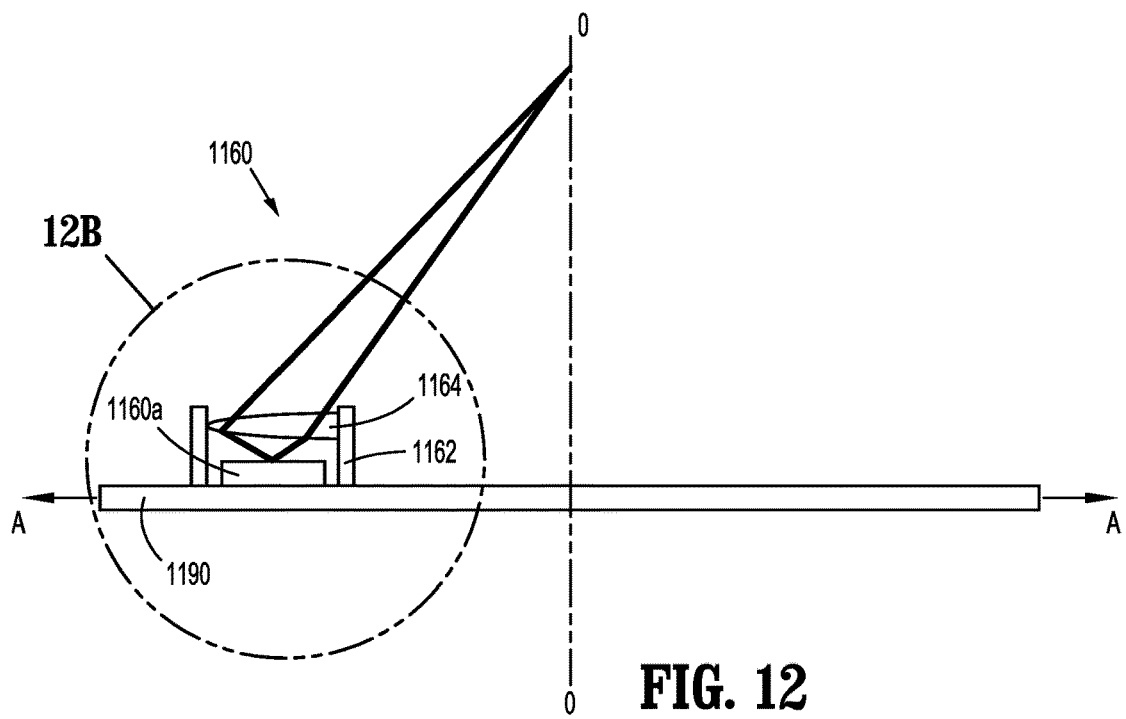
FIG. 12 is a schematic transverse, cross-sectional view of a therapeutic unit of the endoscope of FIGS. 8-11.

With particular reference to FIG. 12, various components of the therapeutic unit 1160 are shown as they relate to one of the plurality of LED light emitting elements. Therapeutic unit 1160 includes an LED light emitting element (e.g., 1160a) engaged with light source substrate 1190, a lens barrel 1162 extending distally from light source substrate 1190, and a lens 1164 disposed within lens barrel 1162. As shown, lens 1164 is configured to focus the light emitted from LED light emitting element 1160a onto one point along the optical axis "0." The optical axis is along or parallel to the longitudinal axis "x." Accordingly, all of the light energy from each LED light emitting element 1160a, 1160b, 1160c, for example, can focus the light on a small area of tissue.

In particular, to help focus the light toward a particular point, a first or proximal surface 1164a of the lens 1164 is disposed at first angle $\alpha 1$ with respect to a first axis "A" which is perpendicular to the optical axis "0," and a second or distal surface 1164b of the lens 1164 is disposed at a second angle $\alpha 2$ with respect to the first axis "A." In disclosed embodiments, each of the first angle $\alpha 1$ and the second angle $\alpha 2$ is between about 5° and about 15° (approximately equal to about 10°). It is envisioned that the first angle $\alpha 1$ and the second angle $\alpha 2$ are functions of the distance of LED light emitting element (e.g., 1160) from the optical axis "0." That is, the first angle $\alpha 1$ and the second angle $\alpha 2$ are larger as the distance from the optical axis "0" increases. It is also envisioned that the first angle $\alpha 1$ and the second angle $\alpha 2$ are the same value or different values.

Figure 12A:
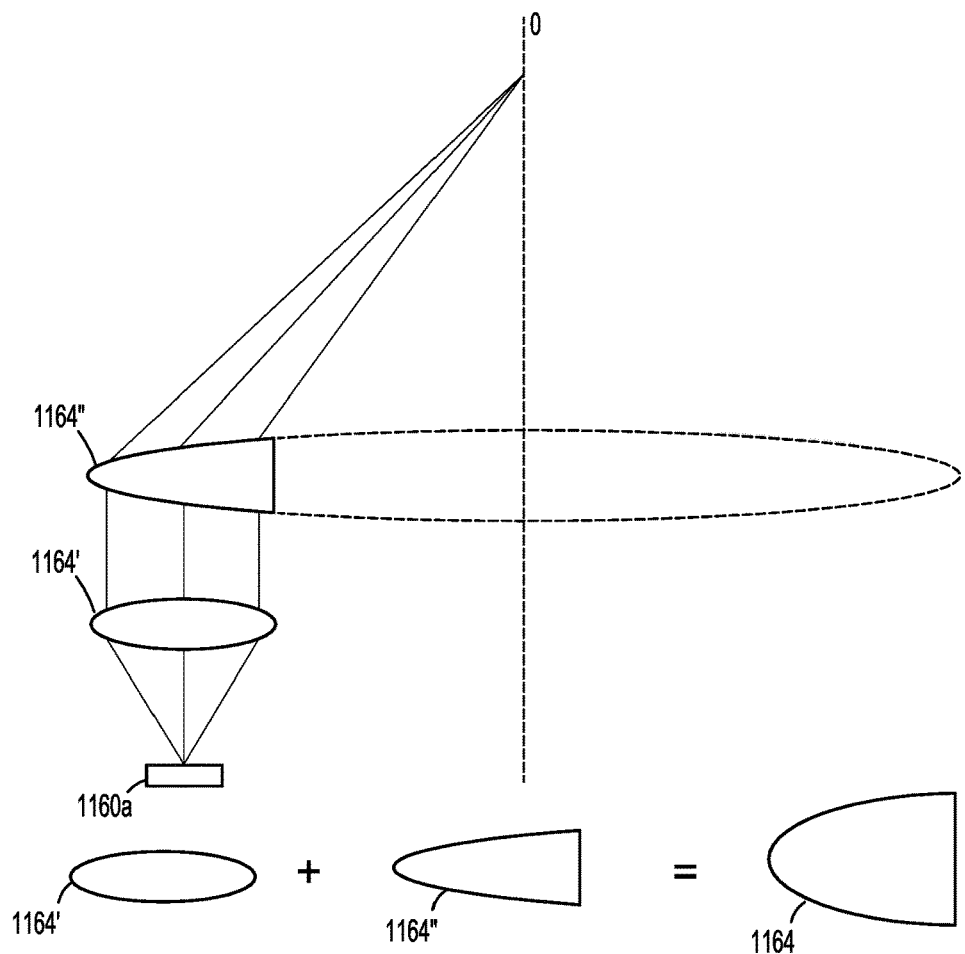
FIG. 12A is a schematic diagram illustrating an overlay of two spherical lenses for use with the therapeutic unit of the endoscope of FIGS. 8-12.
Figure 12B:
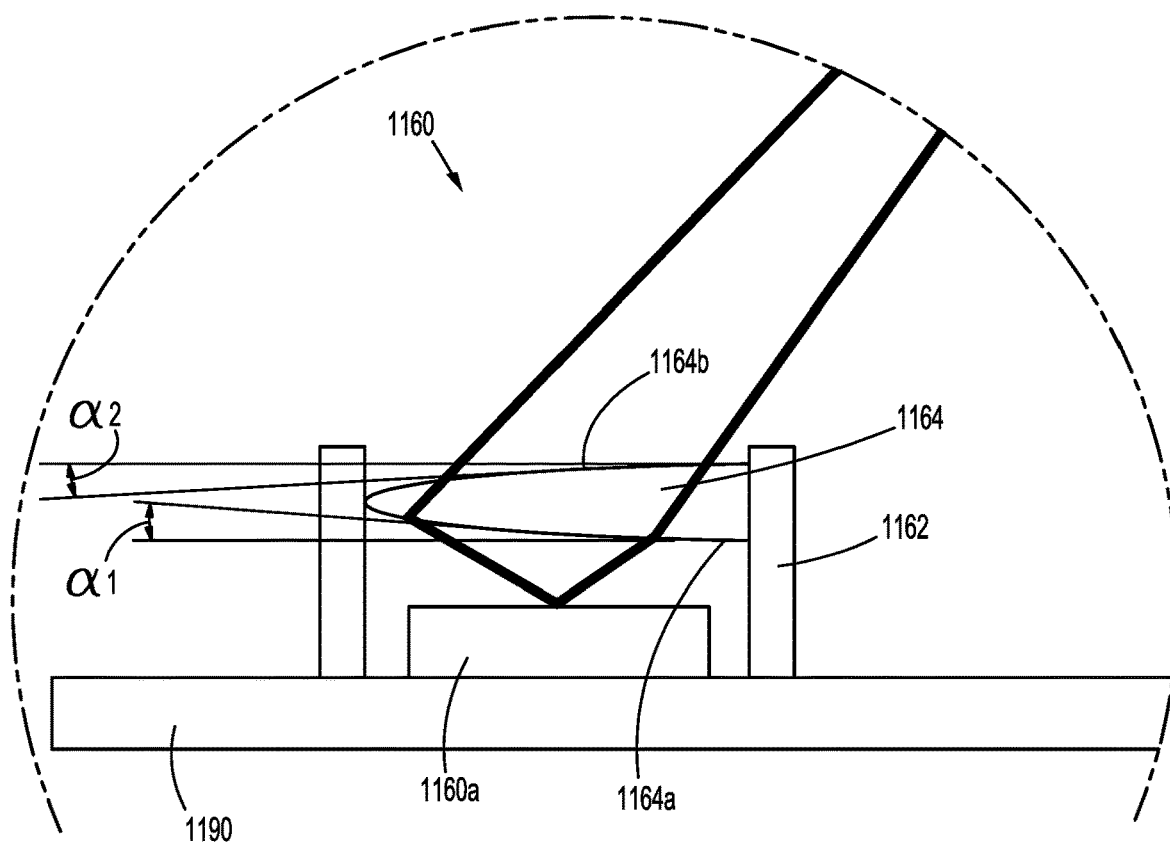
FIG. 12B is an enlarged view of the area of detail indicated in FIG. 12.

One disclosed way of determining the shape of the lens 1164 is schematically illustrated in FIG. 12A. This method involves overlaying a first spherical lens 1164' and a second spherical lens 1164". The first spherical lens 1164' has its center aligned with a center of LED light emitting element 1160a and collimates the light from LED light emitting element 1160a to propagate in a direction that is parallel with the optical axis "0." It is envisioned that the LED light emitting element 1160a is located on the focus of the first spherical lens 1164'. The second spherical lens 1164" has its center aligned with the optical axis "0" and focuses the collimated light which has passed the first spherical lens 1164' to a point along the optical axis "0." It is envisioned that this point along the optical axis "0" is the focus of the second spherical lens 1164". Lens 1164 is thus formed by overlaying the first spherical lens 1164' and a portion of the second spherical lens 1164" (as shown in FIG. 12A).

Endoscope 1110 is configured to illuminate tissue, help a clinician view tissue, and/or to provide therapeutic treatment to tissue. When in use or open, therapeutic unit 1160 is configured to focus it light energy on a small area of tissue (relative to the amount of tissue that is illuminated by light source 1150). The tissue that is focused on absorbs the light energy from the therapeutic unit 1160 and thus increases in temperature. As the temperature of this tissue increases, some of the components of the tissue, such as protein, are broken down, which can have healing effects.

Since different parts of tissue have different absorption rates with respect to different wavelengths of lights, therapeutic unit 1160 can be controlled to produce light within various wavelengths for different healing effects. For example, when at least one LED light emitting element 1160a-1160c of therapeutic unit 1160 emits light with a wavelength raging from about 500 nm to about 600 nm, the blood within the tissue will coagulate from absorbing the light energy as the blood has a large absorption coefficient in this wavelength range (see FIGS. 14 and 15). Meanwhile, other components of tissue have a low absorption coefficient within this wavelength range which results in their temperature increasingly slowly and are thus not greatly influenced.

As another example, LEDs with a central wavelength of about 570 nm (e.g., corresponding to the color red) are able to induce fresh blood cells to produce strong fluorescence in living tissue. Further, red LEDs may be useful in providing therapy for relatively deep tissue (e.g., about 1 mm to about 5 mm from the tissue surface, approximately equal to about 3 mm) as the light within such a wavelength range has a larger penetration depth than ultraviolet light, for instance.

As yet another example, LEDs with a central wavelength of about 650 nm are able to kill gangrene cells.

Light energy produced by therapeutic unit 1160 can also be absorbed by cells and enhance the immunity features of white blood cells, for example.

The present disclosure also relates to method of treating tissue using endoscope 1110. The method includes using the light source 1150 of endoscope 1110 to illuminate tissue, using the image sensor 1142 of endoscope 1110 to visualize tissue, and using the therapeutic unit 1160 of endoscope 1110 to treat tissue.

It will be understood that various modifications may be made to the embodiments described herein. Therefore, the above description should not be construed as limiting, but merely as exemplifications of various embodiments. Those skilled in the art will envision other modifications within the scope and spirit of the claims appended thereto.

What is claimed is:

1. An endoscope comprising:
   a handle;
   an elongated body extending distally from the handle and defining a longitudinal axis, the elongated body including a distal portion;
   a source of light disposed within the distal portion of the elongated body and configured to illuminate tissue; and
   a therapeutic unit disposed within the distal portion of the elongated body and configured to treat tissue, the therapeutic unit including a light emitting element and a lens, the lens of the therapeutic unit is offset from the longitudinal axis and disposed distally of the light emitting element of the therapeutic unit, the lens of the therapeutic unit is configured to focus light emitted from the light emitting element of the therapeutic element towards the longitudinal axis, the lens of the therapeutic unit is formed by overlaying a portion of a first spherical lens and a portion of a second spherical lens, wherein:
   a center of the first spherical lens is offset from the longitudinal axis; and
   a center of the second spherical lens is axially aligned with the longitudinal axis.

2. The endoscope according to claim 1, wherein the therapeutic unit includes a plurality of LED elements.

3. The endoscope according to claim 1, further comprising a controller disposed in electrical communication with the source of light and with the therapeutic unit.

4. The endoscope according to claim 1, further comprising an image sensor disposed within the distal portion of the elongated body and configured to capture a plurality of images.

5. The endoscope according to claim 1, wherein the therapeutic unit is configured to focus the light energy on an area of tissue that is smaller than an area of tissue illuminated by the source of light.

6. The endoscope according to claim 1, wherein the therapeutic unit is configured to emit light having a wavelength ranging from about 500 nm to about 650 nm.

7. The endoscope according to claim 1, wherein the therapeutic unit includes one red light, one blue light and one green light.

8. The endoscope according to claim 1, wherein the source of light includes at least one light emitting diode.

9. The endoscope according to claim 1, wherein the lens of the therapeutic unit is configured to focus the light emitted from the light emitting element of the therapeutic element onto one point.

10. The endoscope according to claim 1, wherein the center of the first spherical lens is axially aligned with a center of the light emitting element.

* * * * *